(12) United States Patent
Shinozaki et al.

(10) Patent No.: US 7,119,192 B2
(45) Date of Patent: Oct. 10, 2006

(54) STRESS-INDUCED PROMOTER DERIVED FROM RICE

(75) Inventors: Kazuko Shinozaki, Ibaraki (JP); Koji Katsura, Ibaraki (JP); Yusuke Ito, Ibaraki (JP)

(73) Assignee: Bio-oriented Technology Research Advancement Institution, Saitama (JP)

( * ) Notice: Subject to any disclaimer, the term of this patent is extended or adjusted under 35 U.S.C. 154(b) by 423 days.

(21) Appl. No.: 10/391,414

(22) Filed: Mar. 18, 2003

(65) Prior Publication Data

US 2005/0278799 A1    Dec. 15, 2005

(30) Foreign Application Priority Data

Dec. 26, 2002  (JP)  ............................. 2002-377316

(51) Int. Cl.
   *C12N 15/82*  (2006.01)
   *A01H 5/00*  (2006.01)
(52) U.S. Cl. .................. 536/24.1; 800/298; 435/320.1; 435/252.3; 435/419
(58) Field of Classification Search ............... 536/24.1; 435/320.1, 252.3, 419; 800/298
   See application file for complete search history.

(56) References Cited

U.S. PATENT DOCUMENTS

| 6,417,428 B1 * | 7/2002 | Thomashow et al. ........ 800/260 |
| 6,495,742 B1 | 12/2002 | Shinozaki et al. |
| 6,670,528 B1 | 12/2003 | Shinozaki et al. |
| 2005/0235381 A1 | 10/2005 | Shinozaki et al. |

FOREIGN PATENT DOCUMENTS

| JP | 2000/060558 | 2/2000 |
| JP | 2000/116260 | 4/2000 |
| JP | 2003219891 | 8/2003 |

OTHER PUBLICATIONS

Menke F.L. et al. A novel jasmonate- and elicitor-responsive element in the periwinkle secondary metabolite biosynthetic gene Str interacts with a jasmonate- and elicitor-inducible AP2-domain transcription factor, ORCA2. EMBO J. Aug. 16, 1999;18(16):4455-63.*

Garcia A. et al. GenBank ACCESSION Z25811, O.sativa salT gene, Jan. 28, 1999.*

Garcia A. et al. The expression of the salt-responsive gene salT from rice is regulated by hormonal and developmental cues. Planta. Dec. 1998;207(2):172-80.*

Y. Yoshiba, et al., Stress-Responsive and Developmental Regulation of Δ1-Pyrroline-5-carboxylate Synthetase 1 (P5CS1) Gene Expression in *Arabidopsis thaliana*, Biochemical and Biophysical Research Communications (BBRC), vol. 261, No. 3, pp. 766-772, Aug. 11, 1999.

Y. Yoshiba, et al., Correlation between the induction of a gene for Δ1-Pyrroline-5-carboxylate Synthetase and the Accumulation of Proline in *Arabidopsis thaliana*, The Plant Journal, vol. 75, No. 5, pp. 751-760, Jan. 20, 1995.

T. Taji et al., Important roles of drought-and cold-inducible genes for galactinol synthase in stress tolerance in *Arabidopsis thaliana*, The Plant Journal, vol. 29, No. 4, p. 417-26, Feb. 2002.

Q. Liu, et al., Two Transcription Factors, DREB1 and DREB2, with an EREBP/AP2 DNA Binding Domain Separate Two Cellular Signal Transduction Pathways in Drought- and Low-Temperature-Responsive Gene Expression, Respectively, in *Arabidopsis*, Plant Cell, vol. 10, pp. 1391-1406, Aug. 1998.

J. Dubouzet et al., OsDREB genes in rice, *Oryza saliva* L., encode transcription activators that function in drought1, high salt- and cold-responsive gene expression, The Plant Journal, vol. 33, p. 751-63, Feb. 2003.

S. Iuchi et al., Regulation of drought tolerance by gene manipulation of 9-cis-epoxycarotenoid dioxgenase, a key enzyme in abscisic acid biosynthesis in *Arabidopsis*, The Plant Journal, vol. 27, p. 325-33, Aug. 2001.

* cited by examiner

*Primary Examiner*—Cynthia Collins
(74) *Attorney, Agent, or Firm*—Davidson, Davidson & Kappel, LLC

(57) ABSTRACT

The invention relates to an isolated stress-induced promoter which effectively functions in monocotyledonous plants such as rice, and of environmental stress tolerant plants using the promoter.

7 Claims, 8 Drawing Sheets

Northern analysis on each stress

Fig. 2

```
        10          20          30          40          50          60
CAACAACCAC  TACTGAACAC  GGCTAAGTGT  GTTTCCTCTC  CTCGAAGATG  TCGTTATTGC
        70          80          90         100         110         120
GTTCTTTTCT  GCTATTCCAT  ACATATCAAT  CTCTAGAGGA  ACACCTTACT  CTAGCTTTCA
       130         140         150         160         170         180
GACAAGGGAC  GGTGGTAAAT  CACGTCGTAT  CCTCCATGGG  GTGTGCTCCG  AAAAACCTTC
       190         200         210         220         230         240
CCTCATGCAT  TAGAGATCAT  GGGTGGAATT  TAGCGATGGC  ACACCTTATT  TATAATTTAG
       250         260         270         280         290         300
TTACTCTCCG  GCGGTACCAT  CTGCTTCCGT  TTGTTGATCG  ATGCTGGCGA  TGATGTGTGT
       310         320         330         340         350         360
GAGTATCGAT  CAACAGAATG  ATCGGACGCT  ATTTTTGGGG  TCGTTTTTTT  TCAGCATTGA
                      Myb
       370         380         390         400         410         420
GGAGGGATGA  GGATTGCTTG  CAACATGCAG  GTGCTGCTCA  AAACAACGGT  TAAGCAGATA
                                    Myc                        MybX2
       430         440         450         460         470         480
TCCGTCAATT  TGATAGTAAG  ATCTGTAACG  CGTGGTCTTT  CGAGCTGAAA  ACTATGGACT
       490         500         510         520         530         540
CTTTGAAACA  AAGATAATAT  TATATTAAAT  TCTATTATTC  AAAGATATCT  AAATATTTAG
       550         560         570         580         590         600
AAAGATATTA  ATAATGTTAT  TAAACTTTGA  CTTACTTAAA  ACAAGTCCAA  AACTGCATGT
       610         620         630         640         650         660
CCCTAAATCG  CCAGAAGATA  AGGAACACCT  GTACCCGTGA  TAACAGAGGG  GTATGAAATT
                                     Myc                  Myb
       670         680         690         700         710         720
TGGACACGAG  GCTTCTTTGG  CAGACGTGGC  GCTGAGTGAG  CTTGGCTCGC  TTGGTCAAAC
       730         740         750         760         770         780
TCCGTGCAGG  GACATTCAGT  TAGCTAGCTA  GCAGCATTGT  CGACAATAAG  ATAGCCTTTA
                          Myb
       790         800         810         820         830         840
AATGTTAGCA  CTCACCAGCT  TGTCAAAAAC  CAAGGCTTGG  TGACGGCGGC  TTCAGAATGA
       850         860         870         880         890         900
AGGATAGATG  GATAAATGTC  TAGAATATTA  TAAAGTCCAA  CAAAAGATGG  AGCACATGCA
       910         920         930         940         950         960
TGAAAGATTA  CGTACACGAA  TGCAGTTGAT  ACAGTGGATG  TTAGGCATAA  GAAGCACTAT
  Sph                        Myb
       970         980         990        1000        1010        1020
AAATAGAGGG  TGCAATCCCC  ATTGCCCTAC  ACAACTACAC  AAGTCGACTA  TCATTACAAG
 TATA
      1030        1040        1050        1060        1070        1080
GAAATTTAAG  CGACCACGAA  GGTATGAAAG  CATAGCAGTA  CTCTGCATTT  TTTTTTTTTG
                                 Intron
      1090        1100        1110        1120        1130        1140
ATGTTGTTCT  AGCTAGCTCT  GCTTAAGGTT  TTCCTTTCTT  TCGTTCTTTG  TTTTTTTTTT
      1150        1160        1170        1180        1190        1200
GTAAGCTCAA  CTAGTTGCAT  GCAATTTAGA  TTTTATCCTT  TTACAGTTGG  AAAAACATCC
      1210        1220        1230        1240        1250        1260
CTATAAATAT  TACCATGAAT  GCATAGAGAT  TCGAGGAAGC  TACAAATTGG  ACGACTGATT
      1270        1280        1290        1300        1310        1320
CCAAAAAAAA  AAAAAAAATC  AGATGGTCAC  ATCATTGCTA  TTGTTTTGTG  AAAGTACAAA
      1330        1340        1350        1360        1370        1380
AGCACTCGTT  CGGATTCAAA  TTACTTGTGC  AAATTAATTA  AAAACCATAG  AAATGATCAT
      1390        1400        1410        1420        1430        1440
GTTACCCCTA  CACATTTCGG  AAACAATACC  ATATATGTTA  GTGTGGGATC  ATTCAAATTG
      1450        1460        1470        1480        1490        1500
ATTTATATCT  GAACAAAACT  GAGTGGGAAT  ACGGTGAGCA  AACTTGACGA  TTCCAAAATA
      1510        1520        1530        1540        1550        1560
ATTTATATTT  AGGCAAAATT  TTACAACTTC  AAAGTTCAAA  CAAGCTAACC  TGAAAAATCA
      1570        1580        1590        1600        1610        1620
TGTTTGAATT  TACTAAGATG  TGCTTTTGTA  TTTACTAAAC  AGAGTATGAC  GCTGGTGAAG
                                   Intron                       ORF
ATTGGT
```

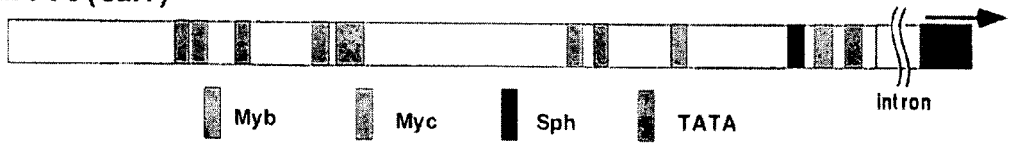

Structure of a2660 (salT) promoter region

Fig. 3

```
-1507  AAGCTTAGGTGTAGTGATAAGAAAAATCGAGAAGGATTGGTACAAGTTAACAACTTAATC  -1448
-1447  AATAGATTGTGCATATAGCAAACAAGTCTATATAATAACACAAAGAGAAAGAAAGAAGAC  -1388
-1387  CCATTTTAGTTGATAGTGGTATTATTACCCAAAAATTAAAAATACGTTCAATTTAGACCT  -1328
            MYB
-1327  ACTTTTATAAGCATCATGCCAGCTACAGCTACAGTCACAGCCTCTTTCATCCCTTTTTCT  -1268
-1267  TTCTTCCAAAAAACGCTCACCTGTAGTGATGGATCTATGTGAAAGTTGTGAGGTCGAATG  -1208
                       MYC
-1207  TCGAATGACCCTACAGCTTCTTCACATTCATTCTTGAGTACTAAATTTTTCATGGAAATC  -1148
-1147  CATTCAAATCTACACAAATAATCCCACTGAAATATTTAATAATAATAATCGATCTCACAA  -1088
-1087  AGTAACTTTATCTAATAATTTATTGACTCCGCCACTGAATTTAAGTGTAGTGATAAAAAA  -1028
-1027  TCGAGAAGAAGGTTTGGTGCAAATTAACAACTTAAACATGAAATTAAATTGTACATGTAG  -968
-967   CAAACAACCTTTATAATAACACAAAAAAAACCATTTTAGTTGAAAGTGGTATTGCTAAAA  -908
                                            MYB
-907   GAGTTAAAAGTATTTCAATTTAGAGCAACATGCCAGCTACGGCTACAGTCACAACCCCTT  -848
-847   TATCCTTTTTCTTTCTTCCAAAATACAAACGCTTACCTTACAGTGATGGTTCTATGTCAA  -788
-787   AGCTGTGGGGTCCGTTGACCCCATAGTTTCTTACCATCATCGTTTAGAGTTTCTTAAATT  -728
                 MYB
-727   TTCTATATTTATCCGTTGAAATTTACACAAATAATCCCACTAAAATATATAGTAATGATA  -668
                 MYB
-667   ATCGATGTCACAGAGTAAATTTGCTGGCTCTGCCACTACTCACCTGTAACCCCCCAACTA  -608
                                             MYC
-607   TGCCACCAAACACACATAACTCATCGCCTCATCATCGTCATCTATCTCCGCATGAGACCG  -548
-547   CATCCTTATCCCACCACGTCCCCCTCGCGCTCACGCGCACAGCAACAAAGAAAAAAAAAA  -488
-487   AAACCGTCCCTTTTCCCTCGCCGCCCCACCGCTCCCCCACCCCACGTGTCGGCGGCCCA  -428
                                                ABRE
-427   TCGGCGGCGGCGCCTGCGTGGGCCGTGTGGCCCACCCTGCGGCCCCTTCCCGAAAACGGA  -368
-367   ACGCCCCCCCCTCCTCCCCTCTCCACGTCACTGCGCGGTGGGCCCGCGCGTGCGTCCAA  -308
-307   GAAGCGTGACGTAAGCAGTGACAGAATCCGCGCCGCCTCTCGGGGCGCCCACGTGTCGCG  -248
                                                        ABRE
-247   GTCAAACGGTCAGCGCGGGGCGGGGGCTCGCATCGCATCTGCTCCACGTGTGCGGCTATCG  -188
                                       MYC     MYC
-187   CGGCTGCGGCCGCACGGGCCACACGTGTCGCTTGCCCCCGGCTCTATAAATGCCCGGCTC  -128
                       ABRE                    TATA box
-127   CTCACCCGGAACAAGTTTCAAGCCCTCCTCTCCTCTTCCCAACACTAGTAGGATAAAGCC  -68
-67    ACAGAGAGAGCAGTAGTAGTAGCGAGCTCGCCGGAGAACGGACGATCACCGGAGAAGGGG  -8
-7     GAGAGAGATG  3
                  Translation start
```

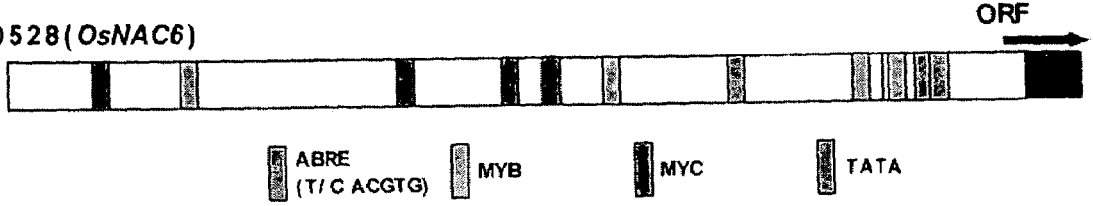

Structure of a0528 (OsNAC6) promoter

Fig. 4
a2660(salT) pro-Gus expression construct
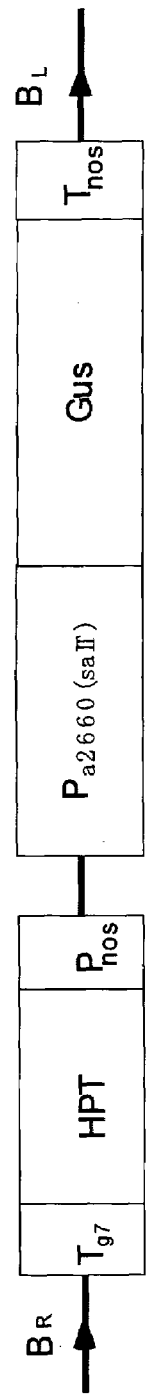
a0528(OaNAC6) pro-Gus expression construct
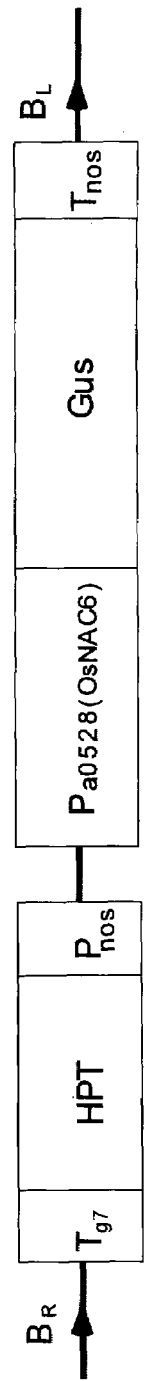
Gus expression construct Leaf Root control          Treated with salt Gus staining after treating salT pro-Gus with salt

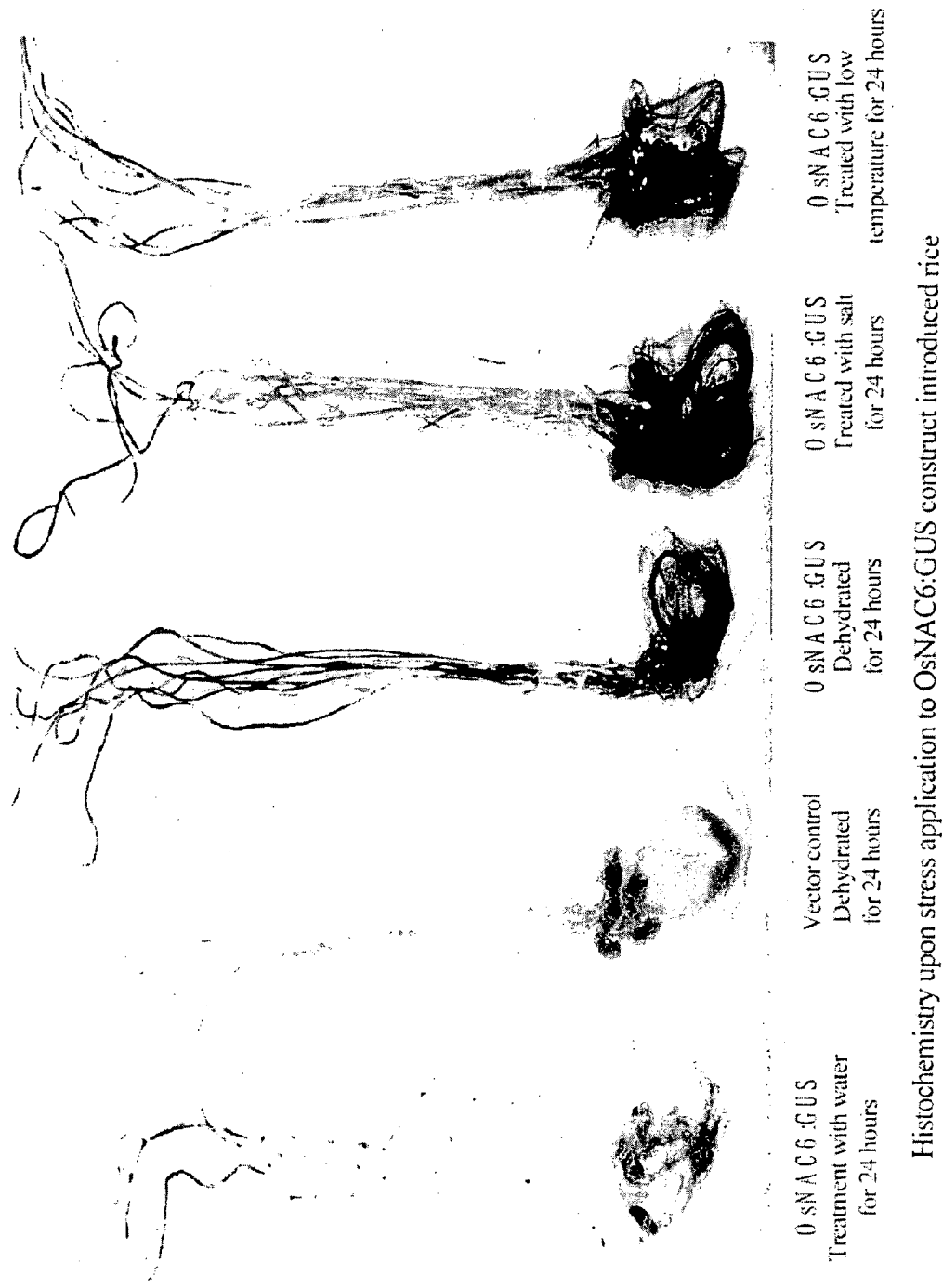

SEQUENCE LISTING

```
<160> NUMBER OF SEQ ID NOS: 11

<210> SEQ ID NO 1
<211> LENGTH: 1608
<212> TYPE: DNA
<213> ORGANISM: Oryza sativa
<220> FEATURE:
<223> OTHER INFORMATION: Inventor: Shinozaki, Kazuko; Katsura, Koji;
      Ito, Yusuke

<400> SEQUENCE: 1
caacaaccac tactgaacac ggctaagtgt gtttcctctc ctcgaagatg tcgttattgc      60
gttcttttct gctattccat acatatcaat ctctagagga acaccttact ctagctttca    120
gacaagggac ggtggtaaat cacgtcgtat cctccatggg gtgtgctccg aaaaaccttc    180
cctcatgcat tagagatcat gggtggaatt tagcgatggc acaccttatt tataatttag    240
ttactctccg gcggtaccat ctgcttccgt ttgttgatcg atgctggcga tgatgtgtgt    300
gagtatcgat caacagaatg atcggacgct atttttgggg tcgtttttttt tcagcattga    360 ggagggatga ggattgcttg caacatgcag gtgctgctca aaacaacggt taagcagata    420
tccgtcaatt tgatagtaag atctgtaacg cgtggtcttt cgagctgaaa actatggact    480
ctttgaaaca aagataatat tatattaaat tctattattc aaagatatct aaatatttag    540
aaagatatta ataatgttat taaactttga cttacttaaa acaagtccaa aactgcatgt    600
ccctaaatcg ccagaagata aggaacacct gtacccgtga taacagaggg gtatgaaatt    660
tggacacgag gcttctttgg cagacgtggc gctgagtgag cttggctcgc ttggtcaaac    720
tccgtgcagg gacattcagt tagctagcta gcagcattgt cgacaataag atagccttta    780
aatgttagca ctcaccagct tgtcaaaaac caaggcttgg tgacggcggc ttcagaatga    840
aggatagatg gataaatgtc tagaatatta taaagtccaa caaagatgg agcacatgca    900 tgaaagatta cgtacacgaa tgcagttgat acagtggatg ttaggcataa gaagcactat    960
aaatagaggg tgcaatcccc attgccctac acaactacac aagtcgacta tcattacaag   1020
gaaatttaag cgaccacgaa ggtatgaaag catagcagta ctctgcattt ttttttttg    1080 atgttgttct agctagctct gcttaaggtt ttcctttctt tcgttctttg ttttttttt    1140
```

-continued

| | |
|---|---|
| gtaagctcaa ctagttgcat gcaatttaga tttatccctt ttacagttgg aaaaacatcc | 1200 |
| ctataaatat taccatgaat gcatagagat tcgaggaagc tacaaattgg acgactgatt | 1260 |
| ccaaaaaaaa aaaaaaaatc agatggtcac atcattgcta ttgttttgtg aaagtacaaa | 1320 |
| agcactcgtt cggattcaaa ttacttgtgc aaattaatta aaaaccatag aaatgatcat | 1380 |
| gttacccta cacatttcgg aaacaatacc atatatgtta gtgtgcgatc attcaaattg | 1440 |
| atttatatct gaacaaaact gagtgggaat acggtgagca aacttgacga ttccaaaata | 1500 |
| atttatattt aggcaaaatt ttacaacttc aaagttcaaa caagctaacc tgaaaaatca | 1560 |
| tgtttgaatt tactaagatg tgcttttgta tttactaaac agagtatg | 1608 |

<210> SEQ ID NO 2
<211> LENGTH: 1520
<212> TYPE: DNA
<213> ORGANISM: Oryza sativa

<400> SEQUENCE: 2

| | |
|---|---|
| ctcccctacg aagcttaggt gtagtgataa gaaaaatcga aaggattgg tacaagttaa | 60 |
| caacttaatc aatagattgt gcatatagca aacaagtcta tataataaca caaagagaaa | 120 |
| gaaagaagac ccattttagt tgatagtggt attattaccc aaaaattaaa aatacgttca | 180 |
| atttagacct acttttataa gcatcatgcc agctacagct acagtcacag cctctttcat | 240 |
| ccctttttct ttcttccaaa aaacgctcac ctgtagtgat ggatctatgt gaaagttgtg | 300 |
| aggtcgaatg tcgaatgacc ctacagcttc ttcacattca ttcttgagta ctaaattttt | 360 |
| catggaaatc cattcaaatc tacacaaata atcccactga aatatttaat aataataatc | 420 |
| gatctcacaa agtaacttta tctaataatt tattgactcc gccactgaat ttaagtgtag | 480 |
| tgataaaaaa tcgagaagaa ggtttggtgc aaattaacaa cttaaacatg aaattaaatt | 540 |
| gtacatgtag caaacaacct ttataataac acaaaaaaaa ccattttagt tgaaagtggt | 600 |
| attgctaaaa gagttaaaag tatttcaatt tagagcaaca tgccagctac ggctacagtc | 660 |
| acaaccccctt tatccttttt ctttcttcca aaatacaaac gcttaccta cagtgatggt | 720 |
| tctatgtcaa agctgtgggg tccgttgacc ccatagtttc ttaccatcat cgtttagagt | 780 |
| ttcttaaatt ttctatattt atccgttgaa atttacacaa ataatcccac taaaatatat | 840 |
| agtaatgata atcgatgtca cagagtaaat ttgctggctc tgccactact cacctgtaac | 900 |
| ccccaacta tgccaccaaa cacacataac tcatcgcctc atcatcgtca tctatctccg | 960 |
| catgagaccg catccttatc ccaccacgtc cccctcgcgc tcacgcgcac agcaacaaag | 1020 |
| aaaaaaaaaa aaacccgtcc cttttccctc gccgccccac cgctcccca ccccacgtgt | 1080 |
| cgccggccca tcggcggcgg cgcctgcgtg ggccgtgtgg cccaccctgc ggcccttcc | 1140 |
| cgaaaacgga acgccccccc cctcctcccc tctccacgtc actgcgcggt gggcccgcgc | 1200 |
| gtgcgtccaa gaagcgtgac gtaagcagtg acagaatccg cgccgcctct cggggcgccc | 1260 |
| acgtgtcgcg gtcaaacggt cagcgcgggg cggggctcg catcgcatct gctccacgtg | 1320 |
| tgcgctatcg cggctgcggc cgcacgggcc acacgtgtcg cttgccccg gctctataaa | 1380 |
| tgcccggctc ctcacccgga acaagtttca agccctcctc tcctcttccc aacactagta | 1440 |
| ggataaagcc acagagagag cagtagtagt agcgagctcg ccggagaacg gacgatcacc | 1500 |
| ggagaagggg gagagagatg | 1520 |

<210> SEQ ID NO 3
<211> LENGTH: 545

```
<212> TYPE: DNA
<213> ORGANISM: Oryza sativa

<400> SEQUENCE: 3
cgactatcat tacaaggaaa tttaagcgac cacgaagagt atgacgctgg tgaagattgg      60
tccgtgggcc ggaaatggag ggtcagctca ggacatcagt gtgccaccca agaagctgtt    120
aggcgtgaca atctacagct cagatgcaat cagatccatt gccttcaact acatcggtgt    180
ggatggacag gaatatgcca ttggtccatg gggtggggc gaaggcacct ctacagagat    240
taaactgggc tcctctgagc agatcaagga gatttctgga acccatggcc cagtctatga    300
tctggctgac attgtcacct atcttaagat tgtgacaagt gctaataata catacgaggc    360
tggagtccca aatggaaagg aattcagcat tccactgcaa gactctggcc atgtcgttgg    420
attctttgga aggtctggaa cgcttatcga cgcaattggc atctacgtcc acccttgatt    480
cccagtggtc aaagaattac tacctactac catatctacg aaataatgtt ccatggtgtt    540
gttgt                                                                545

<210> SEQ ID NO 4
<211> LENGTH: 1423
<212> TYPE: DNA
<213> ORGANISM: Oryza sativa

<400> SEQUENCE: 4
tcgacccacg cgtccgctct tcccaacact agtaggataa agccacagag agagcagtag     60
tagtagcgag ctcgccggag aacggacgat caccggagaa gggggagaga gatgagcggc    120
ggtcaggacc tgcagctgcc gccgggggttc cggttccacc cgacggacga ggagctggtg    180
atgcactacc tctgccgccg ctgcgccggc ctccccatcg ccgtccccat catcgccgag    240
atcgacctct acaagttcga tccatggcag cttccccgga tggcgctgta cggagagaag    300
gagtggtact cttctccccc gcgagaccgc aagtacccga acgggtcgcg ccgaaccgc     360 gccgccgggt cggggtactg gaaggcgacc ggcgccgaca agccggtggg ctcgccgaag    420
ccggtggcga tcaagaaggc cctcgtcttc tacgccggca aggcgcccaa gggcgagaag    480
accaactgga tcatgcacga gtaccgcctc gccgacgtcg accgctccgc ccgcaagaag    540
aacagcctca ggttgatga ttgggtgctg tgccggattt acaacaagaa gggcgggctg    600
gagaagccgc cggccgcggc ggtggcggcg gcggggatgg tgagcagcgg cggcggcgtc    660
cagaggaagc cgatggtggg ggtgaacgcg cggtgagct cccgccgga gcagaagccg     720 gtggtggcgg ggccggcgtt cccggacctg gcggcgtact acgaccggcc gtcggactcg    780
atgccgcggc tgcacgccga ctcgagctgc tcggagcagg tgctgtcgcc ggagttcgcg    840
tgcgaggtgc agagccagcc caagatcagc gagtgggagc gcaccttcgc caccgtcggg    900
cccatcaacc ccgccgcctc catcctcgac cccgccggct ccggcggcct cggcggcctc    960
ggcggcggcg gcagcgaccc cctcctccag gacatcctca tgtactgggg caagccattc   1020
tagacgacca aaaaaaaaaa aaaacaaccg cattggcagc aatggtgtca ctgaacaccg   1080
tgcaggctag ctagcttcat ggccggtgaa ctttgactca ggcgagccgc cggagttgac   1140
tcaaagataa ttaaagaag tgtttttaagt ggattggatt ggattagaca gaggagatga   1200
ggactcgaga aaggcggcga tgagaccgtg gttgggggga ccctggcctg gactgaacga   1260
cgacgaggca gcagcagaaa gatggtgcaa ttgcatcggg tggcatgtca gtgtgtgtgt   1320
atagtggcat gtacatagta catggtgatt gattcggtat acaggggggct agctttcctg   1380
```

-continued tttctgttta aaaaaaaaaa aaaaaaaaaa aaaaaaaaaa aaa    1423

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 5 ctccectacg aagcttaggt agt    23

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 6
aaggatcctc tctcccctt ctccggt    27

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 7
gccagaagct taggaacacc tgtacccg    28

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 8
cagcgggatc tctgtttag taaatac    27

<210> SEQ ID NO 9
<211> LENGTH: 940
<212> TYPE: DNA
<213> ORGANISM: Arabidopsis thaliana

<400> SEQUENCE: 9
gccatagatg caattcaatc aaactgaaat ttctgcaaga atctcaaaca cggagatctc    60
aaagtttgaa agaaaattta tttcttcgac tcaaaacaaa cttacgaaat ttaggtagaa    120
cttatataca ttatattgta attttttgta acaaaatgtt tttattatta ttatagaatt    180
ttactggtta aattaaaaat gaatagaaaa ggtgaattaa gaggagagag gaggtaaaca    240
ttttcttcta ttttttcata ttttcaggat aaattattgt aaaagtttac aagatttcca    300
tttgactagt gtaaatgagg aatattctct agtaagatca ttatttcatc tacttctttt    360
atcttctacc agtagaggaa taaacaatat ttagctcctt tgtaaataca aattaatttt    420
cgttcttgac atcattcaat tttaatttta cgtataaaat aaaagatcat acctattaga    480
acgattaagg agaaatacaa ttcgaatgag aaggatgtgc cgtttgttat aataaacagc    540
cacacgacgt aaacgtaaaa tgaccacatg atgggccaat agacatggac cgactactaa    600
taatagtaag ttacatttta ggatggaata aatatcatac cgacatcagt ttgaaagaaa    660

```
agggaaaaaa agaaaaaata aataaaagat atactaccga catgagttcc aaaaagcaaa      720
aaaaaagatc aagccgacac agacacgcgt agagagcaaa atgactttga cgtcacacca      780
cgaaaacaga cgcttcatac gtgtcccttt atctctctca gtctctctat aaacttagtg      840
agaccctcct ctgttttact cacaaatatg caaactagaa aacaatcatc aggaataaag      900
ggtttgatta cttctattgg aaagaaaaaa atctttggaa                            940

<210> SEQ ID NO 10
<211> LENGTH: 835
<212> TYPE: DNA
<213> ORGANISM: Cauliflower mosaic virus

<400> SEQUENCE: 10
agattagcct tttcaatttc agaaagaatg ctaacccaca gatggttaga gaggcttacg       60
cagcaggtct catcaagacg atctacccga gcaataatct ccaggaaatc aaataccttc      120
ccaagaaggt taagatgca gtcaaaagat tcaggactaa ctgcatcaag aacacagaga       180
aagatatatt tctcaagatc agaagtacta ttccagtatg gacgattcaa ggcttgcttc      240
acaaaccaag gcaagtaata gagattggag tctctaaaaa ggtagttccc actgaatcaa      300
aggccatgga gtcaaagatt caaatagagg acctaacaga actcgccgta aagactggcg      360
aacagttcat acagagtctc ttacgactca atgacaagaa gaaaatcttc gtcaacatgg      420
tggagcacga cacacttgtc tactccaaaa atatcaaaga tacagtctca gaagaccaaa      480
gggcaattga gacttttcaa caagggtaa tatccggaaa cctcctcgga ttccattgcc       540
cagctatctg tcactttatt gtgaagatag tggaaaagga aggtggctcc tacaaatgcc      600
atcattgcga taaaggaaag gccatcgttg aagatgcctc tgccgacagt ggtcccaaag      660
atggaccccc acccacgagg agcatcgtgg aaaaagaaga cgttccaacc acgtcttcaa      720
agcaagtgga ttgatgtgat atctccactg acgtaaggga tgacgcacaa tcccactatc      780
cttcgcaaga cccttcctct ataaggaa gttcatttca tttggagaga acacg            835

<210> SEQ ID NO 11
<211> LENGTH: 927
<212> TYPE: DNA
<213> ORGANISM: Oryza sativa
<220> FEATURE:
<221> NAME/KEY: CDS
<222> LOCATION: (69)..(782)

<400> SEQUENCE: 11
cacactcgag cagagcaaat acagttcagg aatcaggagc aagcagaaac acacacacaa       60 atccgaag atg tgc ggg atc aag cag gag atg agc ggc gag tcg tcg ggg       110
         Met Cys Gly Ile Lys Gln Glu Met Ser Gly Glu Ser Ser Gly
           1               5                  10 tcg ccg tgc agc tcg gcg tcg gcg gag cgg cag cac cag acg gtg tgg       158
Ser Pro Cys Ser Ser Ala Ser Ala Glu Arg Gln His Gln Thr Val Trp
 15                  20                  25                  30 acg gcg ccg ccg aag agg ccg gcg ggg cgg acc aag ttc agg gag acg       206
Thr Ala Pro Pro Lys Arg Pro Ala Gly Arg Thr Lys Phe Arg Glu Thr
                 35                  40                  45 agg cac ccg gtg ttc cgc ggc gtg cgg cgg agg ggc aat gcc ggg agg       254
Arg His Pro Val Phe Arg Gly Val Arg Arg Arg Gly Asn Ala Gly Arg
             50                  55                  60 tgg gtg tgc gag gtg cgg gtg ccc ggg cgg cgc ggc tgc agg ctc tgg       302
Trp Val Cys Glu Val Arg Val Pro Gly Arg Arg Gly Cys Arg Leu Trp
 65                  70                  75
```

```
                                                         -continued ctc ggc acg ttc gac acc gcc gag ggc gcg gcg cgc gcg cac gac gcc      350
Leu Gly Thr Phe Asp Thr Ala Glu Gly Ala Ala Arg Ala His Asp Ala
        80                  85                  90 gcc atg ctc gcc atc aac gcc ggc ggc ggc ggc ggg gga gca tgc          398
Ala Met Leu Ala Ile Asn Ala Gly Gly Gly Gly Gly Gly Ala Cys
 95                 100                 105                 110 tgc ctc aac ttc gcc gac tcc gcg tgg ctc ctc gcc gtg ccg cgc tcc      446
Cys Leu Asn Phe Ala Asp Ser Ala Trp Leu Leu Ala Val Pro Arg Ser
                    115                 120                 125 tac cgc acc ctt cgc cga cgt ccg cca cgc cgt gcc gag gcc gtc gag      494
Tyr Arg Thr Leu Arg Arg Arg Pro Pro Arg Arg Ala Glu Ala Val Glu
                130                 135                 140 gac ttc ttc cgg cgc cgc ctc gcc gac gac gcg ctg tcc gcc acg tcg      542
Asp Phe Phe Arg Arg Arg Leu Ala Asp Asp Ala Leu Ser Ala Thr Ser
            145                 150                 155 tcg tcg tcg acg acg ccg tcc acc cca cgc acc gac gac gac gag gag      590
Ser Ser Ser Thr Thr Pro Ser Thr Pro Arg Thr Asp Asp Asp Glu Glu
        160                 165                 170 tcc gcc gcc acc gac ggc gac gag tcc tcc tcc ccg gcc agc gac ctg      638
Ser Ala Ala Thr Asp Gly Asp Glu Ser Ser Ser Pro Ala Ser Asp Leu
175                 180                 185                 190 gcg ttc gaa ctg gac gtc ctg agt gac atg ggc tgg gac ctg tac tac      686
Ala Phe Glu Leu Asp Val Leu Ser Asp Met Gly Trp Asp Leu Tyr Tyr
                195                 200                 205 gcg agc ttg gcg cag ggg atg ctc atg gag cca cca tcg gcg gcg ctc      734
Ala Ser Leu Ala Gln Gly Met Leu Met Glu Pro Pro Ser Ala Ala Leu
                210                 215                 220 ggc gac gac ggt gac gcc atc ctc gcc gac gtc cca ctc tgg agc tac      782
Gly Asp Asp Gly Asp Ala Ile Leu Ala Asp Val Pro Leu Trp Ser Tyr
            225                 230                 235 tagagctcaa tcaactgtac aattttgcct cttttttctc tcttttctgg cttccgatgc    842
caaaattttg gtactgtacg gacactactt tcggtaatgt gatggaacaa gttgcaaaac    902
aaaaaaaaaa aaaaaaaaaa aaaaa                                          927
```

STRESS-INDUCED PROMOTER DERIVED FROM RICE

BACKGROUND OF THE INVENTION

1. Field of the Present Invention

The present invention relates to a stress-induced promoter derived from rice and a method for using the same.

2. Prior Art

Plants possess tolerance mechanisms to cope with various types of environmental stresses in nature such as dehydration, high temperature, freezing, or salt stress. Recently, as the stress tolerance mechanism is elucidated at a molecular level, stress tolerant plants have been produced using biotechnological techniques. For example, it has been shown that stress proteins such as LEA proteins, water channel proteins, or synthases for compatible solutes are induced in cells when they are exposed to stress, thereby protecting the cells from such stress. Thus, research has been attempted in which genes such as LEA proteins of barley or detoxification enzymes of tobacco, or genes of synthases for osmoregulatory substances (e.g., sugar, proline, or glycinebetaine) are introduced into host plants. Research using genes encoding w-3 fatty acid desaturase of *Arabidopsis thaliana*, the D9-desaturase of blue-green algae, or the like, which are modification enzymes of the cellular membrane lipid, has also been attempted. In the above researches, a gene was bound to the 35S promoter of the cauliflower mosaic virus and introduced into a plant. The level of stress tolerance of the recombinant plant was, however, unstable, and the expression level of the introduced gene was low. Thus, none of these was put to practical use.

On the other hand, stress tolerance mechanism is found to be intricately associated with several genes (Shinozaki K, Yamaguchi-Shinozaki K. Gene Expression and Signal Transduction in Water-Stress Response. Plant Physiol. 1997 October; 115(2) p327–334). Accordingly, research whereby a gene, which encodes a transcription factor and which also simultaneously activates the expression of the genes, is ligated to a constitutive promoter and introduced into a plant, thereby enhancing the plant's stress tolerance, has been attempted (Liu et al., (1998) The Plant Cell, 10:1391–1406). However, when several genes are simultaneously activated, the energy of the host plant becomes directed towards the synthesis of the gene product or intracellular metabolism resulting from the gene product. Accordingly, the growth of the plant itself becomes retarded or dwarf.

SUMMARY OF THE INVENTION

In contrast, the present inventors had isolated the genes DREB1A, DREB1B, DREBIC, DREB2A, and DREB2B encoding the transcription factors which bind to a stress responsive element and specifically activate the transcription of genes located downstream of the element from *Arabidopsis thaliana* (JP Patent Publication (Unexamined Application) No. 2000-60558). They reported that the introduction of the genes in a plant by ligating them with a stress-induced rd29A promoter enabled production of a stress tolerant plant without retarding plant growth (JP Patent Publication (Unexamined Application) No. 2000-116260).

The rd29A promoter is derived from *Arabidopsis thaliana*, a dicotyledonous plant. It is able to function in monocotyledonous plants, however, its activity level is low. Accordingly, a stress-induced promoter capable of high level of activity in monocotyledonous plants has been the object of much research.

An object of the present invention is to discover a stress-induced promoter that can effectively function in monocotyledonous plants such as rice and provide a novel environmental stress tolerant plant that utilizes the promoter.

The present inventors have conducted concentrated studies in order to attain the above object. As a result, they have succeeded in isolating a strong stress-induced promoter from the rice genome. They also found that the environmental stress tolerance of the monocotyledonous plant could be significantly improved with the use of the promoter. This led to the completion of the present invention.

Specifically, the present invention relates to a stress-induced promoter derived from rice. More specifically, the promoter consists of DNA according to (a) or (b) below:
  (a) DNA having the nucleotide sequence as shown in SEQ ID NO: 1 or 2; or
  (b) DNA hybridizing under stringent conditions with DNA having a nucleotide sequence that is complementary to the DNA having a nucleotide sequence as shown in SEQ ID NO: 1 or 2 and expressing stress-induced promoter activity.

The term "stress" used herein refers to dehydration stress, low temperature stress, or salt stress.

The present invention provides a recombinant vector comprising the promoter. The vector may comprise other structural genes or regulator genes under the control of the promoter according to the present invention. It is particularly preferable if the vector comprises structural genes and/or regulator genes for enhancing stress tolerance.

Examples of preferred structural genes for enhancing stress tolerance include the P5CS ($\Delta^1$-pyrroline-5-carboxylate synthetase) gene which is a key enzyme for proline synthesis (Yoshiba Y. et al. (1999) Biochemical and Biophysical Research Communications (BBRC) 261(3), pp. 766–72) and the AtGolS3 (an Arabidopsis galactinol synthase) gene for galactinol synthesis (Taji T. et al. (2002) Plant J Vol 29(4): 417–426).

Examples of preferred regulator genes for enhancing stress tolerance include the Arabidopsis thaliana-derived DREB (dehydration-responsive element binding protein) transcription factor genes (JP Patent Publication (Unexamined Application) No. 2000-60558), the rice-derived OsDREB transcription factor genes (cDNAs for DREB homologs) (Japanese Patent Application No. 2001-358268, Dubouzet et al. The Plant Journal, Volume 33, p. 75 1–63, February 2003), and the NCED (9-cis-epoxycarotenoid dioxygenase) gene which is a key enzyme for the biosynthesis of the plant hormone, ABA, (Juchi S. et al (2001) Plant J. 27: 325–333).

The present invention provides a transformant that is obtained by introducing the vector of the present invention into a suitable host. In one embodiment, the transformant is a transgenic plant that is obtained by introducing the vector of the present invention into a host plant. In this case, the host plant is preferably a monocotyledonous plant, and the monocotyledonous plant is preferably rice.

By introducing the promoter of the present invention into plants, the present invention further provides a process for enhancing stress tolerance in plants. The promoter of the present invention exhibits a potent stress-induced promoter activity which has never been observed in monocotyledonous plants, and thus, the promoter of the present invention is more suitable for enhancing the stress tolerance of monocotyledonous plants.

The present invention is hereafter described in detail.

BRIEF DESCRIPTION OF THE DRAWINGS

FIG. 2 shows the nucleotide sequence of a2660(SalT) in its promoter region.

FIG. 3 shows the nucleotide sequence of a0528(OsNAC6) in its promoter region.

FIG. 4 shows a structure of the Gus expressing construct wherein $T_{g7}$ represents g7 terminator, HPT represents hygromycin phosphotransferase, $P_{nos}$ represents Nos promoter, and $T_{nos}$ represents Nos terminator.

FIG. 8 shows the results of tissue staining for observing GUS expression in transgenic rice prepared by ligating GUS genes to OsNAC6 promoter when various types of stress are applied.

PREFERRED EMBODIMENTS OF THE INVENTION

Figure 1:
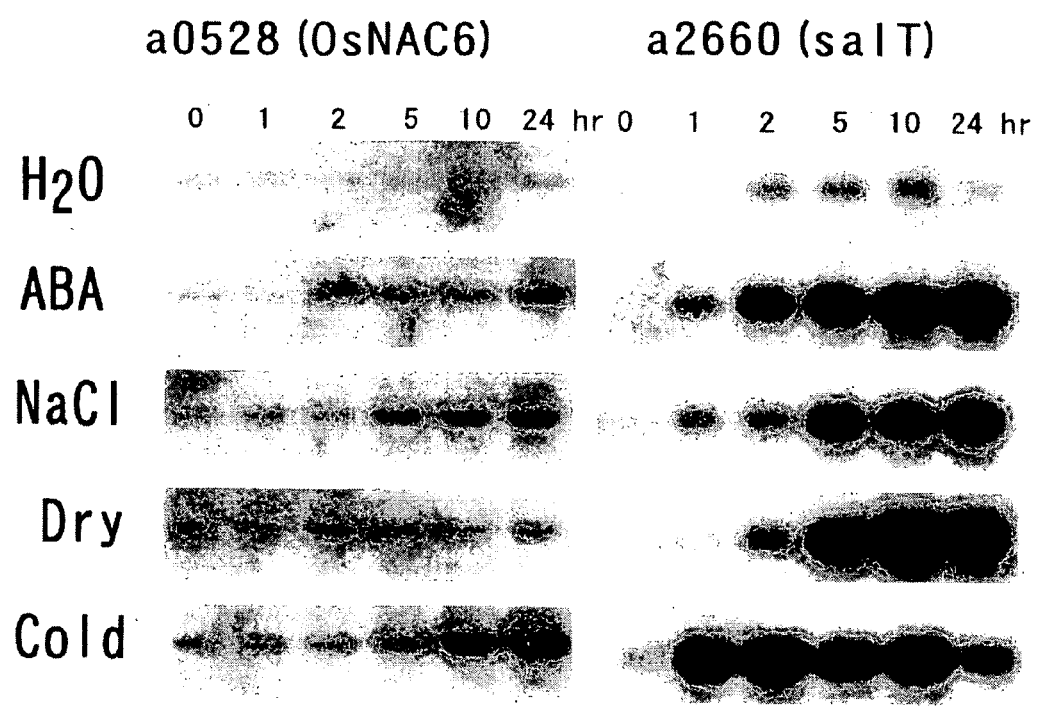
FIG. 1 shows the results of Northern analysis on a0528 (OsNAC6) and a2660(SalT) when each stress is applied.

The promoter of the present invention is an isolated rice-derived promoter, which is induced specifically by environmental stress such as low temperature, dehydration, or salt stress.

1. Identification of the Promoter of the Present Invention

The promoter of the present invention can be identified as follows. Comparing plants which were given stress and plants which were not given stress, the gene which is expressed at a significantly different level (stress-induced gene) is first screened. Subsequently, based on the genome information, a sequence which is considered to be a promoter of the gene is then screened.

A process for identifying the promoter of the present invention is hereafter described.

1.1 Preparation of mRNA

At the outset, mRNA for screening the stress-induced genes is prepared.

As a source of mRNA, parts of the plant such as leaves, stems, roots, or flowers, or the plant as a whole may be used. Alternatively, a plant obtained by sowing seeds on a solid medium such as GM medium, MS medium, or #3 medium and growing them aseptically may be used. The source may be a callus or a cultured cell of the plant which was aseptically grown.

In this screening process, differences in gene expression levels are observed between plants which were given stress and plants which were not given stress. Thus, it is necessary to prepare mRNAs for each of the plants. A method for applying stress is suitably determined depending on the types of plants to be used. In general, dehydration stress can be applied by growing plants without water for 2 to 4 weeks. Low temperature and freezing stresses can be applied by growing plants at 15 to −10° C. for 1 to 10 days. Salt stress can be applied by growing plants in 100 to 600 mM NaCl for 1 hour to 7 days. In the case of rice, for example, hydroponically grown rice is exposed to low temperature stress (10 to −4° C.), salt stress (150 to 250 mM NaCl), and dehydration stress (desiccated state).

Plants which were given stress and plants which were not given stress were frozen with liquid nitrogen and ground in a mortar, etc. From the resultant ground material, a crude RNA fraction is extracted by the glyoxal method, the guanidine thiocyanate and cesium chloride method, the lithium chloride and urea method, the proteinase K and deoxyribonuclease method, or the like. From this crude RNA fraction, poly(A)+ RNA (mRNA) can be then obtained by the affinity column method using oligo dT-cellulose, poly U-Sepharose carried on Sepharose 2B, or the like or by the batch method. The resultant mRNA may further be fractionated by sucrose density gradient centrifugation or the like, if necessary.

1.2 Screening of Stress-Induced Gene

The stress-induced genes are screened based on a comparison of differences in gene expression levels between plants which were given stress and plants which were not given stress. Methods for comparing the gene expression levels are not particularly limited, and specific examples of usable methods include conventional methods such as RT-PCR, real time PCR, subtraction, differential display, differential hybridization, and cross hybridization.

A method using solid phase samples such as gene chips and cDNA microarray is especially suitable for implementing the screening procedure because this method can simultaneously detect the expression of several thousands to several tens of thousands of genes qualitatively and quantitatively.

(1) Preparation of cDNA Microarray

The cDNA microarray used in the screening procedure is not particularly limited as long as the cDNA of the monocotyledonous plant (e.g., rice), i.e., a detection target of the promoter, is spotted thereon. An existing array may be used, or an array may be prepared based on conventional methods (e.g., see The Plant Cell (2001) 13: 61–72 Seki et al).

When preparing the cDNA microarray, the cDNA library of the plant of interest should be prepared first. The cDNA library can be produced by conventional methods using the mRNA prepared in accordance with the method in (1) as a template. The cDNA to be spotted is not particularly limited as long as it is derived from monocotyledonous plants. From the viewpoint of ease in later analyses of genome databases, those derived from monocotyledonous plants such as rice with advanced genome analysis are preferable. Plants may be in a normal state (without treatment). However, plants are preferably exposed to stress such as dehydration, salt, or low temperature.

When producing the cDNA library, a commercially available kit (e.g. ZAP-cDNA Synthesis Kit: Stratagene) is first used for reverse transcription of mRNA and single-stranded cDNA synthesis. Then, double-stranded cDNA is synthesized using the resultant single-stranded cDNA as a template. Subsequently, an adaptor containing a suitable restriction site is added to the resultant double-stranded cDNA, which is then inserted into a cloning site of a lambda phage vector. The resultant DNA is packaged in vitro using a commercially available kit (e.g., Gigapack III Gold packaging extract (Stratagene)) and infected into an *E. coli* host, and then amplified. Thus, the cDNA library of interest can be obtained.

Once the cDNA library is produced, this cDNA or a region with high specificity thereof (e.g., the UTR region containing no repeating sequence on the 3' side) is amplified by PCR to produce a probe to be immobilized on the array.

When probes for all the genes of interest are produced by repeating this procedure, these are spotted on a slide glass using a commercially available spotter (e.g., those manufactured by Amersham). Thus, the cDNA microarray of interest is obtained.

(2) Detection of Gene Expression Level

Gene expression levels can be detected by the cDNA microarray as signal intensity obtained when sample mRNA (or cDNA) labeled with a suitable reagent is hybridized with the cDNA probe on the microarray. In general, the expression level of the gene is preferably determined as a comparative value with a suitable control or the ratio of expression levels between two samples to be considered with respect to the differences in the amount of cDNA probes spotted on the array. In the case of the present screening procedure, mRNA derived from plants which were not given stress (without treatment) is employed as a control, relative to which detected expression levels of mRNA derived from stress-applied plants are reflected as ratio values.

Detection is carried out as follows. mRNAs of the control and the sample (or cDNA thereof) are respectively labeled with different fluorescent dyes (e.g., Cy3 and Cy5) and hybridized with the cDNA probe on the array. For example, mRNA is extracted from the stress-applied plants and subjected to reverse transcription in the presence of Cy5 labeled dCTP to prepare Cy5 labeled cDNA. Subsequently, mRNA is extracted from plants which were not given stress (without treatment), and Cy3 labeled cDNA is prepared in the same manner. Equivalent portions of Cy5 labeled cDNA (sample) and Cy3 labeled cDNA (control) are mixed with each other and hybridized with cDNA on the array. As labeling dyes, Cy3 may be used for the sample, and Cy5 may be used for the control. Alternatively, other suitable label reagents may also be used.

The obtained fluorescence intensity is read using a fluorescent signal detector and then converted into numerical value. This numerical value is equivalent to the ratio of the gene expression levels of the sample relative to the control. The fluorescence intensity read using a scanner is optionally subjected to error adjustment or normalization of variances for each sample. Normalization can be carried out based on the genes that are commonly expressed in each sample such as house keeping genes. Further, a threshold line for reliability may be determined to remove data with low correlation.

(3) Selection of Stress-Induced Genes

Based on the analytical results by the array, stress-induced genes are specified as genes that are expressed at significantly different levels between plants which were given stress and plants which were not given stress. The term "significantly different" used herein refers to, for example, given an intensity level of 1,000 or higher, the difference between two plants is three times or more.

(4) Analysis of Expression by Northern Blotting

The thus selected genes are further subjected to Northern analysis and the like. Thus, the expression levels of the genes are confirmed to be enhanced with respect to stress tolerance levels. For example, plants are exposed to various levels of stress such as salt, dehydration, or temperature in the manner described above. RNA is then extracted from the plant and separated by electrophoresis. The separated RNA is transferred to a nitrocellulose membrane and hybridized with a labeled cDNA probe that is specific for the gene. Thus, the expression level thereof can be detected.

If the expression level of the selected gene is enhanced in a stress-dependent manner, it can be confirmed that the gene is stress-induced. Examples of stress-induced genes selected from the rice cDNA library include a2660 (SalT: SEQ ID NO: 3) and a0528 (OsNAC6: SEQ ID NO: 4). a2660 and a0528 are identification numbers (ID No.) of cDNA immobilized on the micro array.

1.3 Screening of Promoter Sequence (1) Screening from Gene Database

Subsequently, using a detection software (e.g., Blast), existing gene databases (e.g., DDBJ database) are searched for promoter sequences of the stress-induced genes. Regarding a plant such as rice, the genome of which has been mostly decoded, all promoter sequences controlling specified stress-induced genes can be searched for by using existing databases. Promoter sequences are selected as regions that are considered to be promoters from among the upstream regions in genome genes which are highly genomically homologous to the stress-induced gene (cDNA). For example, based on the genome information of stress-induced genes, the region approximately 1 to 2 kb upstream of the site that is presumed to be an initiation codon for these genes is deduced to be a promoter region.

Some of the conventional stress-induced promoters have in their sequences cis elements involved with promoter activities, for example, dehydration responsive elements (DRE), abscisic acid responsive elements (ABRE), and low temperature stress responsive elements. When a stress-induced transcription factor is bound to the cis element, the aforementioned promoter is activated, and the stress tolerance imparting genes which are under control of the promoter are allowed to express. Accordingly, if the cis element is contained in the upstream region that is being searched, this region is highly likely to be a stress-induced promoter.

Thus, a deduced SalT promoter sequence (SEQ ID NO: 1) was screened from the 1.6 kb upstream region of a gene highly homologous to the aforementioned a2660 (SalT: SEQ ID NO: 3), and a deduced OsNAC6 promoter sequence (SEQ ID NO: 2) was screened from 1.5 kb upstream region of a gene highly homologous to a0528 (OsNAC6: SEQ ID NO: 4).

(2) Confirmation of Functionality of Stress-Induced Promoter

Subsequently, the functionality of the deduced promoter sequence is confirmed by changes in promoter activity when stress is applied.

At the outset, a primer is produced based on the promoter sequence deduced in the section above. PCR is carried out using genome DNA as a template, and the promoter is cloned. Subsequently, a reporter gene is ligated downstream of the promoter to produce a reporter plasmid. The produced reporter plasmid is then introduced into a plant, thereby investigating the expression of the reporter gene when stress is applied to the plant (preferably its $T_2$ generation). Examples of reporter genes include β-glucuronidase (e.g., GUS: pBI121, Clontech), luciferase gene, and green fluorescent protein gene. GUS is preferable because its activity can be indicated by numerical values and its expression can be visually observed by staining.

1.4 Promoter of the Present Invention

Based on the above, the rice genome-derived SalT promoter (SEQ ID NO: 1) and the OsNAC6 promoter (SEQ ID NO: 2) were found to be stress-induced promoters which were expressed highly in a dehydration-, low temperature-, or salt stress-dependent manner.

Thus, both the SalT promoter and the OsNAC6 promoter are induced specifically for all stresses. The OsNAC6 promoter comprises the cis sequence, ABA responsive element (ABRE); however, the sequence of the SalT promoter does not comprise a specific cis sequence. The OsNAC6 promoter is rapidly induced by dehydration stress, and the SalT promoter is rapidly induced by low temperature stress.

The promoter of the present invention is not limited to DNA having the nucleotide sequence as shown in SEQ ID NO: 1 or 2. The stress-induced promoter of the present invention includes DNA which hybridizes under stringent conditions with DNA having a nucleotide sequence that is complementary to the DNA having the nucleotide sequence as shown in SEQ ID NO: 1 or 2 as long as the DNA has a stress-induced promoter activity. The term "stringent conditions" as used herein refers to parameters with which the art is familiar. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Nucleic acid hybridization parameters may be found in references which compile such methods, e.g., Molecular Cloning: A Laboratory Manual, J. Sambrook, et al., eds., Second Edition, Cold Spring Harbor Laboratory Press, Cold Spring Harbor, N.Y., 1989. More specifically, stringent conditions, as used herein, refers, for example, to those conditions in which formamide concentration is 30–50%, temperature is 37 to 50° C., and 6×SSC. Preferably, formamide concentration is 50%, temperature is 42° C., and 6×SSC.

2. Recombinant Vector

The recombinant vector of the present invention comprises the promoter of the present invention. The vector may comprise other functional structural genes or regulator genes downstream of the promoter of the present invention. Examples of preferred genes include structural genes and/or regulator genes for enhancing stress tolerance. The term "functional" refers to a state in which other structural genes or regulator genes are suitably expressed under the control of the promoter of the present invention.

Structural genes for enhancing stress tolerance encode a protein which plays roles in enhancing plants' tolerance to environmental stress such as dehydration, low temperature, or salt stress. Examples thereof include: LEA proteins; water channel proteins; synthases for compatible solutes; detoxification enzyme of tobacco; synthases for osmoregulatory substances (e.g., sugar, proline, or glycinebetaine); genes encoding w-3 fatty acid desaturase of *Arabidopsis thaliana* and the D9-desaturase of blue-green algae, which are modification enzymes of the cellular membrane lipid; P5CS which is a key enzyme of proline synthesis; and the AtGolS3 gene for galactinol synthesis.

A regulator gene for enhancing stress tolerance regulates the activity of stress-induced promoter and the expression of genes for imparting stress tolerance, thereby enhancing stress tolerance in plants. Examples thereof include: *Arabidopsis thaliana*-derived transcription factors such as DREB1A, DREB2A, DREB1B, and DREB1C genes (see JP Patent Publication (Unexamined Application) No. 2000-60558); rice-derived transcription factors such as OsDREB1A, OsDREB1B, OsDREB1C, OsDREB1D, and OsDREB2A genes (see Japanese Patent Application No. 2001-358268); and NCED genes which are key enzymes for the biosynthesis of the plant hormone, ABA.

When the promoter of the present invention comprises a specific cis element, the gene of the transcription factor that binds to the cis element and enhances its promoter activity is particularly preferably ligated downstream of the promoter.

The vector of the present invention is constructed to be functional by ligating (inserting) the promoter of the present invention or the promoter and another regulator gene or structural gene to (into) an appropriate vector. The vector into which the promoter is to be inserted is not particularly limited as long as it is replicable in a host. For example, plasmid DNA, phage DNA or the like may be used. Plasmid DNA includes: plasmids for *E. coli* hosts such as pBR322, pBR325, pUC118, and pUC119; plasmids for *Bacillus subtilis* hosts such as pUB 10 and pTP5; plasmids for yeast host such as YEp13, YEp24, and YCp50; and plasmids for plant cell host such as pBI221 and pBI121. Phage DNA includes λ phage and the like. Further, an animal virus vector such as retrovirus or vaccinia virus, or an insect virus vector such as baculovirus may also be used.

The promoter of the present invention is inserted into a vector by cleaving the purified DNA with an appropriate restriction enzyme and then inserted into the restriction site or the multi-cloning site of an appropriate vector for ligation.

The recombinant vector of the present invention may comprise a splicing signal, poly(A) addition signal, selection marker, ribosome binding sequence (SD sequence) or the like, if so desired. Examples of selection marker are dihydrofolate reductase gene, ampicillin tolerance gene, neomycin tolerance gene, or the like.

3. Transformant

The transformant of the present invention can be produced by introducing the recombinant vector of the present invention into a host so that the promoter activity can be expressed. Hosts are not particularly limited as long as the promoter of the present invention can function therein. Preferably, hosts are plants, and the monocotyledonous plants such as rice are particularly preferred.

When plants or plant cells are used as hosts, for example, cells established from rice, maize, wheat, *Arabidopsis thaliana*, tobacco, or carrot or protoplasts prepared from these plants are used. Methods for introducing recombinant vectors into plants include a method by Abel et al, which utilizes polyethylene glycol [Abel, H. et al. Plant J. 5:421-427(1994)], and electroporation.

4. Stress Tolerant Transgenic Plant (1) Production of Transgenic Plant

Structural genes and/or regulator genes for enhancing stress tolerance are introduced into plants so as to locate under the control of the promoter of the present invention. Thus, functional transgenic plants with enhanced tolerance to environmental stress such as low temperature, freezing, or dehydration stress can be produced. Particularly preferred host plants are monocotyledonous plants.

A method for introducing the promoter of the present invention, etc. into a host plant includes indirect introduction such as the *Agrobacterium* infection method and direct introduction such as the particle gun method, polyethylene glycol method, liposome method, and microinjection method. Up to the present, the use of the *Agrobacterium* infection method to produce transgenic plants from monocotyledonous plants such as rice was difficult. However, the addition of acetosyringon enabled *Agrobacterium* to infect rice. Thus, the *Agrobacterium* infection method became usable for monocotyledonous plants.

Production of transgenic plants using *Agrobacterium* is hereafter described.

A recombinant vector to be introduced into a plant can be prepared by cleaving with an appropriate restriction enzyme DNA comprising the promoter of the present invention and a structural gene and/or regulator gene for enhancing stress tolerance, ligating an appropriate linker to the resultant DNA if necessary, and inserting the DNA into a cloning vector for the plant cell host. A binary vector type plasmid such as pBI2113Not, pBI2113, pBI101, pBI121, pGA482, pGAH, and pBIG, or an intermediate vector type plasmid such as pLGV23Neo, pNCAT, and pMON200 may be used as cloning vectors.

When a binary vector type plasmid is used, the gene of interest is inserted between the border sequences (LB, RB) of the binary vector. The resultant recombinant vector is amplified in *E. coli*. The amplified recombinant vector is then introduced into *Agrobacterium tumefaciens* C58, LBA4404, EHA101, C58C1Rif$^R$, EHA105, etc. by freeze-thawing, electroporation, or the like. The resultant *Agrobacterium* is used to transform the plant.

In the present invention, the three-member conjugation method [Nucleic Acids Research, 12:8711 (1984)] may also be used in addition to the method described above to prepare an *Agrobacterium* to be introduced into plants. Specifically, plasmid-containing *E. coli* comprising the gene of interest, helper plasmid-containing *E. coli* (e.g. pRK2013), and an *Agrobacterium* are mixed and cultured on a medium containing rifampicin and kanamycin. Thus, a zygote *Agrobacterium* to be infected into plants can be obtained.

For the expression of a foreign gene, etc. in plant bodies, a terminator for plants, etc. should be located downstream of the structural gene. Specific examples of terminator sequences which may be utilized in the present invention include cauliflower mosaic virus-derived and nopaline synthase gene-derived terminators. Terminators are not limited to the above-mentioned as long as they are known to be functional in plant bodies.

In order to efficiently select transgenic cells of interest, use of an effective selection marker gene is preferable. As the selection marker, one or more genes, which are selected from kanamycin tolerance (NPTII) gene, hygromycin phosphotransferase (htp) gene which confers tolerance to the antibiotic hygromycin on plants, phosphinothricin acetyl transferase (bar) gene which confers tolerance to bialaphos, and the like, can be used. The promoter of the present invention and the selection marker gene may be incorporated together into a single vector. Alternatively, they may be incorporated into separate vectors respectively.

If the plant is infected with the thus prepared *Agrobacterium*, a transgenic plant of interest can be produced.

The transgenic plant is sowed onto a medium containing an adequate antibiotic, and plants containing promoters or genes of interest are selected. The selected plants are transferred to pots containing Bonsol No. 1, black dirt, or the like and are further grown. Generally, the genes are introduced into the genome of the host plant in a similar manner. However, due to differences in the locations on the genome into which the genes have been introduced, the expression of the introduced genes varies. This phenomenon is called a "position effect." By analyzing transformants with DNA fragments from the introduced gene as a probe by Northern blotting, it is possible to select those transformants in which the introduced gene is expressed more highly.

(2) Confirmation of Stress Tolerance

The confirmation that the promoter of the present invention or a structural gene and/or regulator gene for enhancing stress tolerance is integrated in the transgenic plant into which the gene of the present invention has been introduced and in the subsequent generation thereof can be made by extracting DNA from cells and tissues of those plants and detecting the introduced gene by PCR or Southern analysis, which are conventional methods in the art.

The expression level and expression organ of a gene in a transgenic plant can be analyzed by extracting RNA from cells and tissues of the plant and detecting the mRNA of the introduced gene by RT-PCR or Northern analysis, which are conventional methods in the art. Alternatively, the expression level and expression site of the transcription product of the introduced gene can be analyzed directly by Western blotting using an antibody against the above product or the like.

The tolerance to environmental stresses of the transgenic plant into which the promoter of the present invention has been introduced can be evaluated by setting the transgenic plant in a pot containing a soil comprising vermiculite, perlite, Bonsol, and the like or hydroponically growing plants, exposing the plants to various environmental stresses, and examining the survival of the plants. Environmental stresses include low temperature, dehydration, and salt stresses. For example, tolerance to dehydration stress can be evaluated by leaving the plant without water for 2 to 4 weeks and then examining the survival. Tolerance to low temperature and freezing stresses can be evaluated by leaving the plant at 15 to −10° C. for 1 to 10 days, growing it at 20 to 35° C. for 2 days to 3 weeks, and then examining its survival ratio. Tolerance to salt stress can be evaluated by, for example, leaving the plant in 100 to 600 mM NaCl for 1 hour to 7 days, growing it at 20 to 35° C. for 1 to 3 weeks, and then examining its survival ratio.

Thus, use of the promoter of the present invention can significantly enhance stress tolerance without retarding the growth of plants (particularly monocotyledonous plants).

EXAMPLES

The present invention is described in more detail with reference to the following examples, however, the scope of the present invention is not limited to these.

Example 1

Identification of Stress-Induced Rice Gene

The stress-induced rice genes were searched by the cDNA microarray and Northern analysis.

1. Production of Rice cDNA Microarray

Rice seeds (Nihonbare) that were grown hydroponically for 2 to 3 weeks were subjected to dehydration, salt, or low temperature stress. Dehydration stress was applied by air-drying at room temperature, salt stress was applied by culturing in a 250 mM NaCl solution, and low-temperature stress was applied by cultivation at 4° C. The rice which was processed with each stress was frozen with liquid nitrogen. Total RNA was extracted from the frozen sample using the guanidine thiocyanate and cesium chloride method, and mRNA was prepared using the Oligo(dt)-cellulose column. cDNA was synthesized using the resultant mRNA as a template and using HybriZAP-2.1 two-hybrid cDNA Gigapack cloning kit (Stratagene), and the cDNA was inserted and cloned in the EcoRI-XhoI cleavage site of HybriZAP-2.1 phagemid vector. This phagemid DNA was packaged using Gigapack III Gold packaging extract (Stratagene). The obtained lambda phage particles containing cDNA were used to infect into host *E. coli*, which were then amplified, and these were subsequently recovered as a phage suspension.

The nucleotide sequences of the cDNA clones were sequenced to select about 1,500 independent clones. The selected clones were amplified by PCR and stamped onto a poly-L-lysine-coated microslide glass (model S7444, Matsunami) using GTMASS System (Nippon Laser and Electronic Laboratory). Thereafter, the clones were immobilized by UV cross-linking to produce the rice cDNA microarray (The Plant Cell (2001) 13: 61–72 Seki et al.).

2. Microarray Analysis mRNAs were respectively purified from rice plants which were given dehydration, salt, or low temperature stress or treated with 100 μM abscisic acid (5 hours or 10 hours) in the same manner as in the section above and from rice plants that were not given stress. mRNA derived from rice plants without treatment was employed as a control, and mRNA derived from rice plants treated with each stress or abscisic acid was employed as a sample. cDNA microarray analysis was carried out by dual-fluorescent labeling using Cy3 and Cy5. As a result of the microarray analysis, the genes with intensities of 1,000 or higher, namely the genes with expression levels as high as 3 times compared to the control, were selected as candidate stress-induced genes.

3. Expression Analysis by Northern Hybridization

The characteristic expression of the genes selected in the section above was analyzed by Northern hybridization. Rice plants were first exposed to abscisic acid, dehydration, low temperature, salt, or water stress, and sampling was accomplished on stress-applied rice every 0, 1, 2, 5, and 10 hours. The abscisic acid, dehydration, low temperature, and salt stresses were respectively applied in the same manner as in 1., and water stress was applied by immersing the plants in pure water. Total RNA was prepared from each sample, electrophoresis was carried out, and the expression of each gene was observed by the Northern method. The results are shown in FIG. 1.

As is apparent from FIG. 1, the expressions of the a0528 gene (OsNAC6: SEQ ID NO: 3) and the a2660 gene (SalT: SEQ ID NO: 4) were induced by the abscisic acid-, dehydration-, low temperature-, salt-, or water-stress. In particular, the expression of a0528 was rapidly induced by dehydration stress, and that of a2660 was rapidly induced by low temperature stress.

Example 2

Screening of Promoter Sequence

1. Screening of Rice Genome Database

Using blast, the rice genome database of DDBJ was searched for homologous sites of cDNA:a0528 (OsNAC6: SEQ ID NO: 3) and a2660 (SalT: SEQ ID NO: 4) that were selected as stress-induced genes in Example 1. As a result, in the gene in which homology was observed, the sequence located 1.5 kb upstream of the initiation codon toward the 5' side of the gene was selected as a promoter sequence of a0528, and the sequence located 1.6 kb upstream of the gene was selected as a promoter sequence of a2660 (SEQ ID NO: 1 and SEQ ID NO: 2, respectively).

Structures of each of the promoter regions are shown in FIG. 2 and FIG. 3. While OsNAC6 has the cis sequence ABA responsive element (ABRE), SalT does not have a specific cis sequence in the promoter sequence.

2. Cloning

Based on the selected promoter sequences, primers were designed, PCR was carried out using rice genome DNA as a template, and cloning was carried out. The primer sequences and the conditions for PCR used are as follows.

Primer Sequences:

```
                                            (SEQ ID NO: 5)
    OsNAC Forward:   ctcccctacgaagcttaggtagt (SEQ ID NO: 6)
    OsNAC Reverse:   aaggatcctctctccccttctccggt (SEQ ID NO: 7)
    SalT Forward:    gccagaagcttaggaacacctgtacccg (SEQ ID NO: 8)
    SalT Reverse:    cagcgggatcctctgtttagtaaatac
```

PCR conditions: 30 cycles of 95° C. for 1 minute, 55° C. for 1 minute, and 68° C. for 2 minutes Example 3

Analysis of Function of SalT Promoter

The promoter site of pBIG29APHSNot was substituted with an ubiquitin promoter of maize to produce G-ubi plasmid. The G-ubi plasmid was cleaved with BamHI-HindIII and ligated to a fragment of a similarly cleaved SalT promoter. The plasmid into which the SalT promoter has been incorporated was cleaved with BamHI-EcoRI, and similarly, ligated to the Gus gene, which was cleaved out from pBI221 (Clontech) with BamHI-EcoRI to produce a GUS-expressing construct G-SalT:GUS (FIG. 4). The plasmid G-SalT:GUS was introduced by electroporation into *Agrobacterium* EHA105, which was washed with 10% glycerol after culturing, and thereby preparing *Agrobacterium* EHA105 (G-SalT:GUS) to produce a transformant.

Rice seeds were immersed in 70% ethanol for 1 minute and sterilized by immersion into 2% sodium hypochlorite for 1 hour. The sterilized seeds were then washed with sterilized water, and 9 grains each of the seeds were sowed onto a plate of N6D solid medium (3.98 g of CHU[$N_6$] Basal Salt Mixture (Sigma), 30 g of sucrose, 100 mg of myo-inositol, 300 mg of casamino acid, 2,878 mg of L-proline, 2 mg of glycine, 0.5 mg of nicotinic acid, 0.5 mg of pyridoxine hydrochloride, 1 mg of thiamine hydrochloride, 2 mg of 2,4-D, and 4 g of Gellite, per liter, pH 5.8), followed by culturing for 24 days. Thus, callus was induced. The callus formed from approximately 20 grains of the seeds was transferred to new N6D solid medium, followed by culturing for additional three days.

Separately, *Agrobacterium* EHA105 (G-SalT:GUS), was cultured in 5 ml of YEP medium containing 100 mg/l rifampicilin and 20 mg/l kanamycin (10 g of Bacto peptone, 10 g of Bacto yeast extract, 5 g of NaCl, and 406 mg of $MgCl_2.6H_2O$, per liter, pH 7.2) at 28° C. for 24 hours. This *Agrobacterium* was diluted with AAM medium containing 20 mg/l acetosyringon (10 mg of $MnSO_4.5H_2O$, 3 mg of $H_3BO_3$, 2 mg of $ZnSO_4.7H_2O$, 250 μg of $Na_2MoO_4.2H_2O$, 25 μg of $CuSO_4.5H_2O$, 25 μg of $CoCl_2.6H_2O$, 750 μg of KI, 150 mg of $CaCl_2.2H_2O$, 250 mg of $MgSO_4.7H_2O$, 40 mg of Fe-EDTA, 150 mg of $NaH_2PO_4.2H_2O$, 1 mg of nicotinic acid, 10 mg of thiamine hydrochloride, 1 mg of pyridoxine hydrochloride, 100 mg of myo-inositol, 176.7 mg of L-arginine, 7.5 mg of glycine, 900 mg of L-glutamine, 300 mg of aspartic acid, and 3 g of KCl, per liter, pH 5.2) to bring $O.D._{660}$ to 0.1. Thus, 20 ml of *Agrobacterium* suspension was prepared.

Subsequently, to the callus, which was cultured for 3 days, the *Agrobacterium* suspension was added and then mixed for 1 minute. Thereafter, this callus was placed on a sterilized paper towel to remove excess *Agrobacterium* suspension and then cultured on 2N6-AS solid medium, on which the sterilized filter paper was placed, (3.98 g of $CHU[N_6]$ Basal Salt Mixture, 30 g of sucrose, 10 g of glucose, 100 mg of myo-inositol, 300 mg of casamino acid, 2 mg of glycine, 0.5 mg of nicotinic acid, 0.5 mg of pyridoxine hydrochloride, 1 mg of thiamine hydrochloride, 2 mg of 2,4-D, 10 mg of acetosyringon, and 4 g of Gellite, per liter, pH 5.2) at 25° C. for 3 days in the dark. After culturing for 3 days, the culture product was thoroughly washed with an aqueous solution of 3% sucrose containing 500 mg/l carbenicillin until the product did not whiten. The washed culture product was further cultured on N6D solid medium containing 500 mg/l carbenicillin and 10 mg/1 hygromycin for 1 week. Thereafter, the resulting culture product was transferred onto a N6D solid medium containing 500 mg/l carbenicillin and 50 mg/l hygromycin and cultured for 18 days. Furthermore, the callus was transferred to a redifferentiation medium (4.6 g of Murashige and Skoog Plant Salt Mixture (Nihon Pharmaceutical Co., Ltd), 30 g of sucrose, 30 g of sorbitol, 2 g of casamino acid, 100 mg of myo-inositol, 2 mg of glycine, 0.5 mg of nicotinic acid, 0.5 mg of pyridoxine hydrochloride, 0.1 mg of thiamine hydrochloride, 0.2 mg of NAA, 2 mg of kinetin, 250 mg of carbenicillin, 50 mg of hygromycin, and 8 g of agarose, per liter, pH 5.8). The product was transferred to a new medium every week and redifferentiated. Those having buds grown to approximately 1 cm were transferred to a hormone-free medium (4.6 g of Murashige and Skoog Plant Salt Mixture (Nihon Pharmaceutical Co., Ltd), 30 g of sucrose, 2 mg of glycine, 0.5 mg of nicotinic acid, 0.5 mg of pyridoxine hydrochloride, 0.1 mg of thiamine hydrochloride, 50 mg of hygromycin, and 2.5 g of Gellite, per liter, pH 5.8). Plant bodies, which have grown to approximately 8 cm on the hormone-free medium, were transferred to a pot containing synthetic particulate potting soil (Bonsol No. 1, Sumitomo Chemical Co., Ltd.) to allow the transgenic plant to produce seeds.

The $T_2$ generation of the obtained GUS-expressing transgenic rice was hydroponically grown for 2 weeks and exposed to dehydration stress in the same manner as in Example 1.

Similarly, the rd29A promoter (SEQ ID NO: 9: Nature Biotechnology (1999) 17: 287–291) or the $^{35}S$ promoter (SEQ ID NO: 10) was ligated upstream of the GUS gene to produce constructs. The obtained constructs were introduced into rice and/or tobacco.

In the case of GUS-expressing transgenic tobacco, a plant, which was regenerated from a T1 generation plant, was grown in a plant cone for 3 to 5 weeks, and a grown leaf was bisected. One thereof was determined as a control, and the other was air dried at room temperature and then exposed to dehydration stress.

Figure 5:
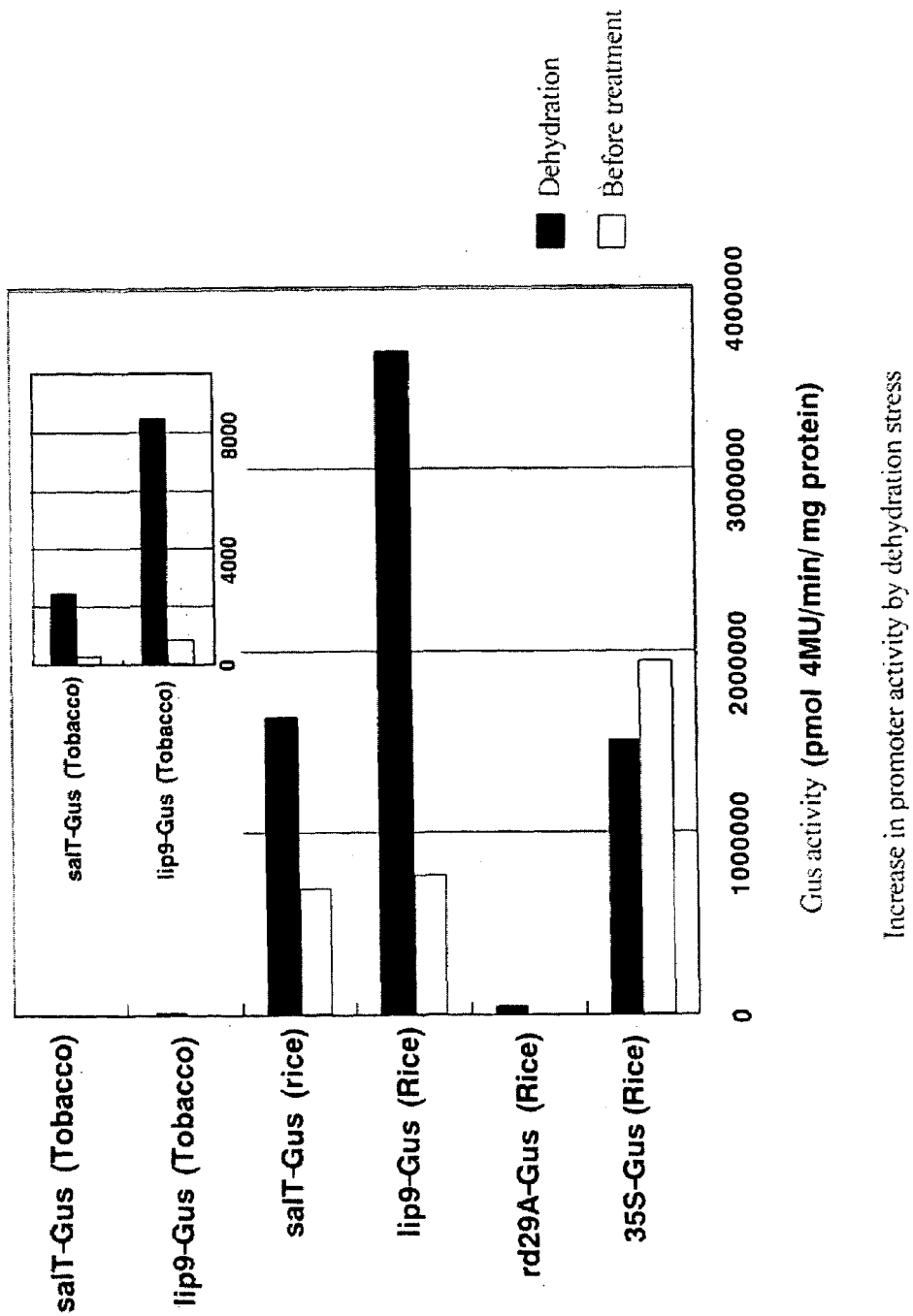
FIG. 5 is a graph showing the GUS activities of transgenic tobacco or rice prepared by introducing various promoters ligated to GUS genes when dehydration stress is applied.

The GUS activities of each transgenic rice and tobacco were assayed based on changes in fluorescence intensities caused by the decomposition of 4-methylumbelliferyl-β-D-glucuronide. FIG. 5 shows the GUS activities of the transgenic plants to which various promoters have been introduced at the time of the application of dehydration stress.

As is apparent from FIG. 5, an activity level of the stress-induced SalT promoter in monocotyledonous plants, i.e., rice is higher than that of rd29A promoter. In contrast, while the SalT promoter also exhibited stress-induced promoter activities in tobacco, a dicotyledonous plant, its activity was weaker than that in rice.

Figure 6:
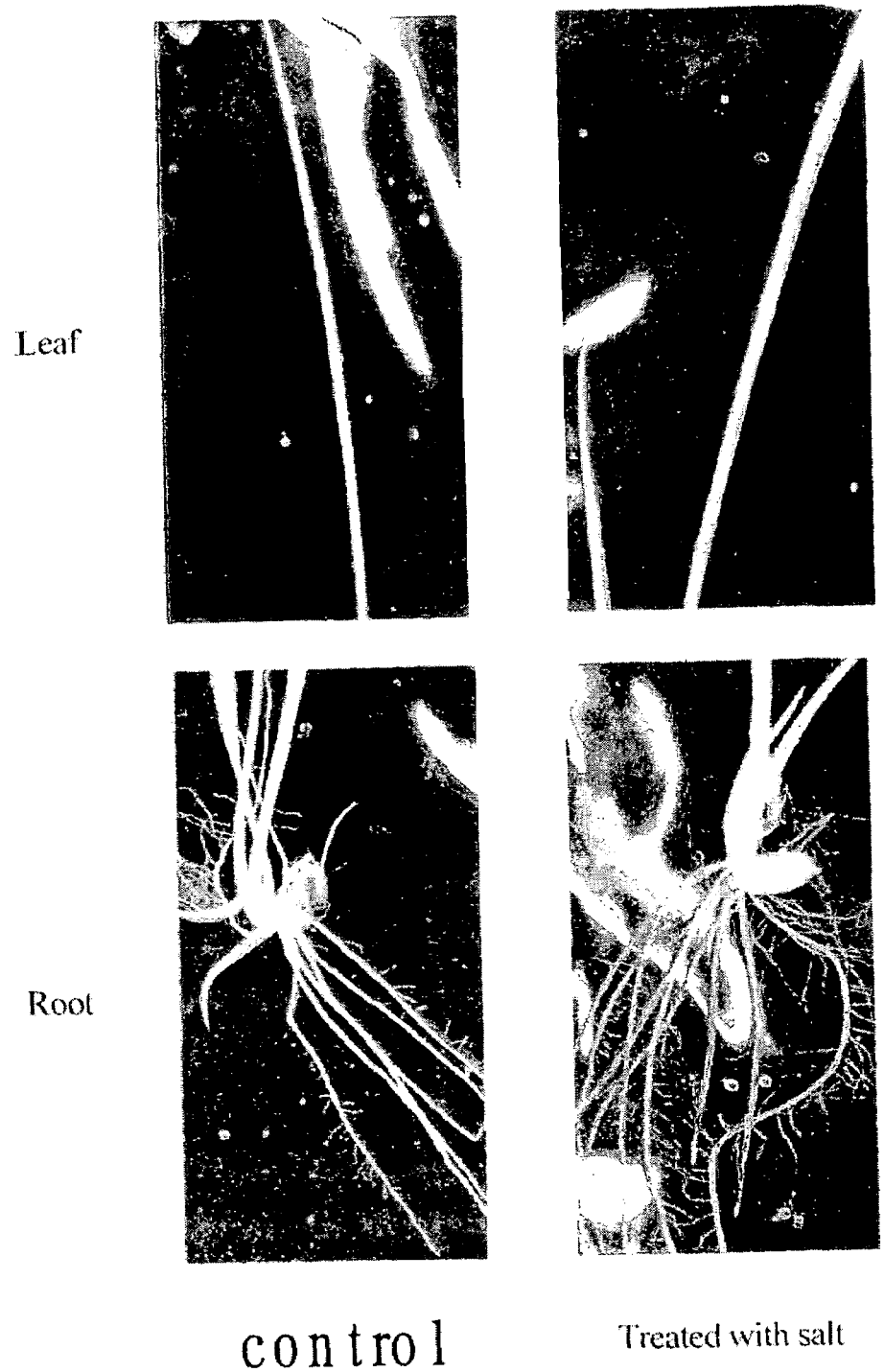
FIG. 6 is a graph showing the results of GUS staining on a transgenic rice prepared by introducing SalT promoter ligated to GUS genes when salt stress is applied.

Further, the entire plant of the rice to which the SalT promoter-GUS construct has been introduced was immersed in salt water and GUS staining was carried out. As a result, the entire plant was stained (FIG. 6). Based on this, SalT promoter was found to function in the entire plant which was given stress.

Example 4

Analysis of Function of OsNAC6 Promoter

The promoter site of pBIG29APHSNot was substituted with an ubiquitin promoter of maize to produce G-ubi plasmid. The G-ubi plasmid was cleaved with BamHI-HindIII and ligated to a fragment of the similarly cleaved OsNAC6 promoter. The plasmid into which the OsNAC6 promoter has been incorporated was cleaved with BamHI-EcoRI, and ligated to the Gus gene, which was similarly cleaved out from pBI221 (Clontech) with BamHI-EcoRI to produce a GUS-expressing construct (FIG. 4). The produced construct was introduced into rice or tobacco using *Agrobacterium* to produce transformants.

Figure 7:
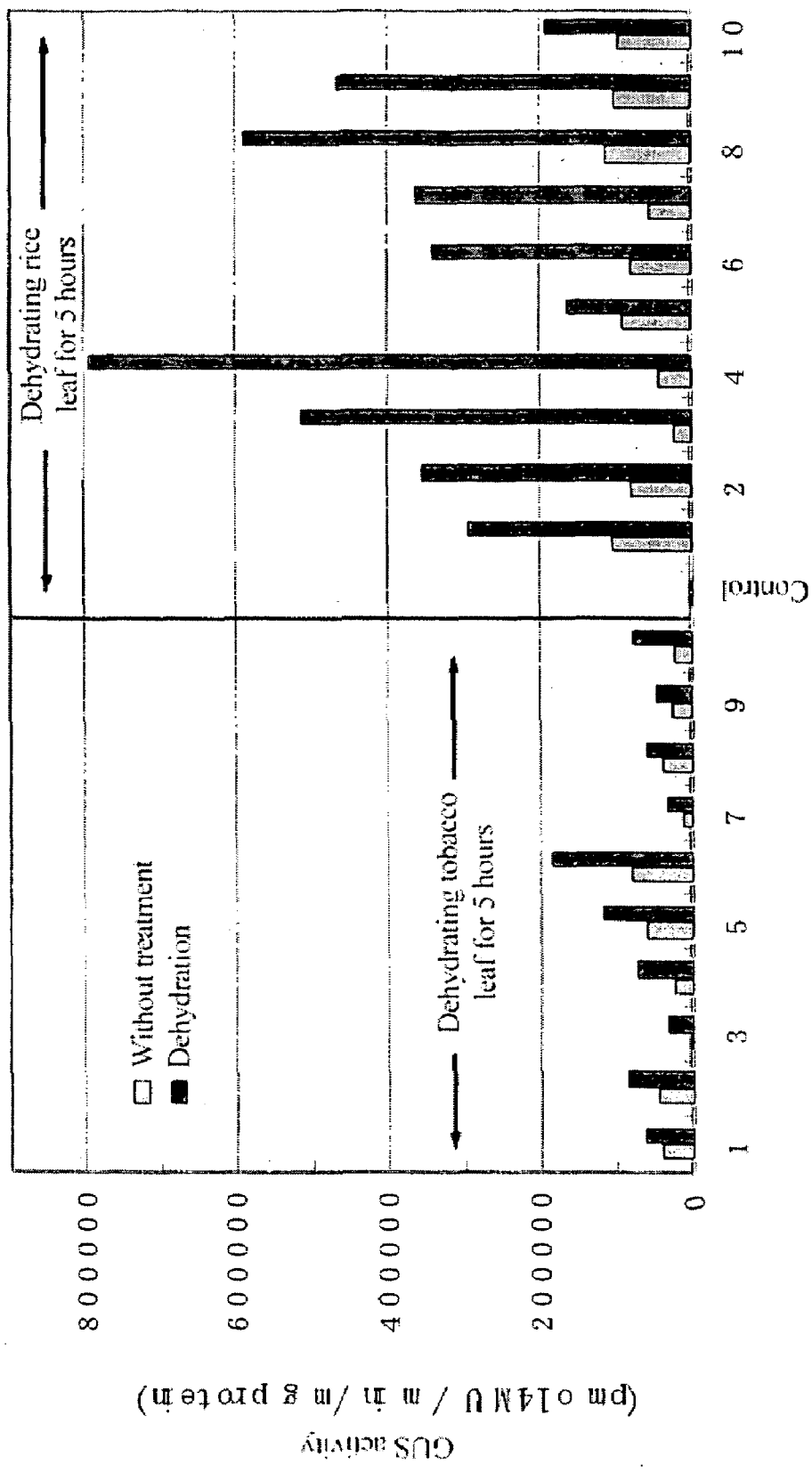
FIG. 7 is a graph showing the GUS activities of transgenic tobacco and rice prepared by introducing OsNAC6 promoter ligated to GUS genes when dehydration stress is applied.

The transgenic tobacco and rice were exposed to dehydration stress in accordance with Example 1, and the GUS activities were assayed in the same manner as in Example 3. As a result, the level of dehydration induced OsNAC6 promoter activity was high (FIG. 7). A level of promoter activity of OsNAC6 was higher in rice than in tobacco. The $T_2$ generation of the transgenic rice was exposed to dehydration, salt, or low temperature stress in accordance with Example 1, and GUS expression in the plant after the application of stress was investigated by tissue staining. As a result, the OsNAC6 promoter was found to express GUS in the entire plant in a dehydration, salt, or low temperature stress-dependent manner (FIG. 8).

Accordingly, the SalT promoter and the OsNAC6 promoter were found to be activated in a stress-induced manner and to allow stress tolerant genes under the control thereof to be expressed. In addition, the level of stress-induced promoter activities of the promoter was so high, the level of which has never before been observed in monocotyledonous plants. Thus, if structural genes and/or regulator genes for enhancing stress tolerance are ligated so as to locate under the control of the promoter of the present invention and introduced into plants, highly stress tolerant transgenic plants can be produced in monocotyledonous plants including important grain plants such as rice.

Reference Example 1

Production of pBE35S:OsDREB1A, G-ubi:OsDREB 1A, and G35S- ShΔ:OsDREB1A

G-ubi and G35S-ShΔ were prepared as follows. At the outset, pBIG plasmid (Nucleic Acids Research 18: 203 (1990)) was cleaved with BamHI, blunt-ended and ligated to delete the BamHI cleavage site. Thereafter the plasmid was cleaved with HindIII and EcoRI. The resultant fragment and an approximately 1.2 kb fragment, which was obtained by cleavage of pBE2113Not plasmid in the same manner, were ligated to each other, thereby preparing pBIG2113Not plasmid.

Subsequently, pBIG2113Not was cleaved with HindIII and BamHI and ligated to a fragment of rd29A promoter (approximately 0.9 kb, Nature Biotechnology 17: 287–291 (1999)), which was cleaved in the same manner, thereby preparing pBIG29APHSNot plasmid. Further, this pBIG29APHSNot plasmid was cleaved with HindIII and SalI and then ligated to a fragment of the ubiquitin gene (Ubi-1) promoter (approximately 2.0 kb, Plant Molecular Biology 18: 675–689 (1992)) of maize or a fragment (approximately 1.6 kb, Proceeding National Academy of Science USA 96: 15348–15353 (1999)) containing CaMV 35S promoter of p35S-shΔ-stop and a part of the intron of a sucrose synthase gene (Sh1) of maize, which was cleaved in the same manner. Thus, G-ubi plasmid or G35S-shΔ plasmid was prepared.

pBE2113Not, G-ubi, and G35S-shΔ described above were cleaved with BamHI and ligated to the similarly cleaved OsDREB1A gene (SEQ ID NO: 11) fragment encoding a transcription factor of rice using Ligation High (Toyobo Co., Ltd.). *E. coli* DH5α was transformed using the thus obtained ligation product. After the transformant was cultured, plasmid pBE35S:OsDREB1A, G-ubi: OsDREB1A, and G35S-ShΔ: OsDREB1A were purified therefrom.

Effect of the Invention

The present invention provides a stress-induced promoter, which is effectively functional in monocotyledonous plants. With the use of this promoter, excellent stress tolerance can be imparted to monocotyledonous plants including grain plants such as rice.

Free Text of Sequence Listing

SEQ ID NO: 5—description of artificial sequence: primer
SEQ ID NO: 6—description of artificial sequence: primer
SEQ ID NO: 7—description of artificial sequence: primer
SEQ ID NO: 8—description of artificial sequence: primer

What is claimed is:

1. An isolated rice-derived promoter consisting of DNA which has the nucleotide sequence as shown in SEQ ID NO: 1.

2. A recombinant vector comprising the promoter according to claim 1.

3. The vector according to claim 2, wherein structural genes and/or regulator genes for enhancing stress tolerance are operably linked to the promoter or transcribed under the control of the promoter.

4. The vector according to claim 3, wherein the structural genes and/or regulator genes for enhancing stress tolerance are selected from the group consisting of P5CS genes which encode a key enzyme for proline synthesis, AtGolS3 genes for galactinol synthesis, Arabidopsis thaliana-derived DREB transcription factor genes, rice-derived OsDREB transcription factor genes, and NCED genes which encode a key enzyme for the synthesis of ABA.

5. A transformant, which is obtained by introducing the vector according to claim 2 into a host.

6. The transformant according to claim 5, wherein the host is a plant.

7. The transformant according to claim 6, wherein the host is a monocotyledonous plant.

* * * * *